(12) United States Patent
Fearon et al.

(10) Patent No.: US 6,238,670 B1
(45) Date of Patent: May 29, 2001

(54) COMPOSITIONS AND METHODS EMPLOYING A LIGAND FOR CD21 OR CD19 FOR MODULATING THE IMMUNE RESPONSE TO AN ANTIGEN

(75) Inventors: Douglas T. Fearon; Paul W. Dempsey, both of Cambridge (GB)

(73) Assignee: Cambridge University Technical Services Limited, Cambridge (GB)

(*) Notice: Subject to any disclaimer, the term of this patent is extended or adjusted under 35 U.S.C. 154(b) by 0 days.

(21) Appl. No.: 08/849,488

(22) PCT Filed: Dec. 6, 1995

(86) PCT No.: PCT/GB95/02851

§ 371 Date: Oct. 21, 1997

§ 102(e) Date: Oct. 21, 1997

(87) PCT Pub. No.: WO96/17625

PCT Pub. Date: Jun. 13, 1996

(30) Foreign Application Priority Data

Dec. 6, 1994 (GB) ................................................ 9424631

(51) Int. Cl.[7] .............................. A61K 39/00; C07K 19/00
(52) U.S. Cl. .................................... 424/192.1; 424/278.1; 514/19; 530/350; 530/380
(58) Field of Search ............................ 424/192.1, 278.1; 514/19; 530/350, 380

(56) References Cited

U.S. PATENT DOCUMENTS 5,225,538 * 7/1993 Capon et al. .
5,331,090 * 7/1994 Lernhardt et al. .
5,866,694 * 2/1999 Katinger et al. .

FOREIGN PATENT DOCUMENTS

| 91/02536 | 3/1991 | (WO) . |
| 91/13974 | 9/1991 | (WO) . |
| 91/16437 | 10/1991 | (WO) . |

OTHER PUBLICATIONS

Klein, Immunology The Science of Self–Nonself Discrimination, Wiiley & Sons, pp. 335, 339, and 343, 1982.*
Griffioen, A. W. et al. Infect. Immun. 59 (5): 1839–1845, May, 1991.*
Mold et al., "CR2 is a Complement Activator and the Covalent Binding Site for C3 During Alternative Pathway Activation by Raji Cells," *The Journal of Immunology*, 140(6):2934–2934 (1988).
Hebell et al., "Suppression of the Immune Response by a Soluble Complement Receptor of B Lymphocytes," *Science*, 254(5028):102–105 (1991).
Dempsey and Fearon, "Creating Supra– and Infra–Immunogenic Forms of Antigen by Fusion with C3d," 9th International Congress of Immunology, p. 581, Jul. 23–29, 1995.

* cited by examiner

*Primary Examiner*—David Saunders
*Assistant Examiner*—Amy DeCloux
(74) *Attorney, Agent, or Firm*—Flehr Hohbach Test Albritton & Herbert LLP; Richard F. Trecartin

(57) ABSTRACT

Described herein are compositions which modulate the immune response. In one aspect, a composition is described which comprises an antigen covalently linked to a ligand for CD21(CR2) or CD19. This antigen is not associated with a complement C3 fragment through an ester bond derived from the internal thioester of the complement C3 fragment.

38 Claims, 10 Drawing Sheets

HEL

HEL-C3d

HEL-C3d$_2$

HEL-C3d$_3$

*C1028/S1028

COMPOSITIONS AND METHODS EMPLOYING A LIGAND FOR CD21 OR CD19 FOR MODULATING THE IMMUNE RESPONSE TO AN ANTIGEN

The present invention relates to administration of immunogens and modulation, either inhibition or augmentation, of the immune response.

The initial encounter with antigen is the most difficult phase of an immune response. The threshold for activating unprimed, as opposed to primed, T cells is higher and B cells express unmutated, generally low affinity antigen receptors. This can be problematic when there is a need or desire for raising an immune response to an immunogen of interest, for example for therapeutic purposes or in order to obtain antibodies for subsequent manipulation and use.

The Complement system plays a major role in enhancing the immune response. Almost twenty years ago Pepys showed that depleting mice of C3 decreased their immune response to sheep erythrocytes, as measured by their antibody response to this antigen (1). Subsequent studies of humans, guinea pigs and dogs with genetically determined deficiencies of C3 or of C4 and C2, the proteins that form the enzymes that activate C3, confirmed the conclusion that activation of C3 augmented the primary immune response (2).

C3 is a plasma protein that contains a thioester that mediates covalent attachment to other biological molecules (3). Activation of C3 to C3b by a "C3 convertase" of the classical or alternative pathway makes the thioester accessible to attack by weak nucleophiles such as the —OH or carbohydrates, causing attachment of C3b, via an ester linkage, to target—OH—bearing molecule in the immediate vicinity of the activation reaction. C3b (or proteolytically processed fragments iC3b and C3dg) complexes with antigen then binds receptors CR1, CR2 and CR3. Binding of the complexes to C3 receptors on follicular dendritic cells in the primary follicles and germinal centres of secondary lymphoid organs may promote development and maintenance of memory B lymphocytes. Binding of the complexes to antigen-specific B lymphocytes causes cross-linking of CR2 to the antigen receptor, membrane immunoglobulin (mIg). CR2 is associated with the B lymphocyte membrane protein CD19 which amplifies signalling through mIg by approximately 100-fold when coligated to it.

A limiting step in this overall reaction is the attachment of C3b. It requires the antigen be capable of activating the Complement system, through either the classical or the alternative pathway, and that it have a site to which C3b can covalently attach. Problems then arise when the immunogen of interest is, for instance, a soluble peptide and protein, since these tend not to be activators of the alternative pathway nor effectively to bind C3b. Furthermore, low affinity, cross-reactive IgM antibodies do not bind monovalent protein antigens with sufficient avidity to activate the classical pathway.

These difficulties may be especially relevant when immunising with small peptides, for example that have been defined as epitopes for B or T cells, and with DNA immunisation (4). Although adjuvants may be used to enhance immunogenicity of peptides and non-aggregated proteins when immunising experimental animals such as mice, in general their administration to humans is not possible or at least not preferred.

The present invention now provides a way of enhancing the immune response to an immunogen.

Additionally, there are circumstances when it is desirable to inhibit, ie at least reduce, the immune response to an immunogenic substance. For instance, there is much interest in the administration of therapeutic antibodies. Historically, however, the antibodies available have been murine monoclonal antibodies. Because the human body recognises such murine antibodies as foreign an immune response is mounted against them, resulting in their rapid clearance from the bloodstream. Numerous techniques of "humanising" non-human antibodies and other techniques for reducing their foreign character are available but often require highly-skilled workers to perform them. Furthermore, even following "humanisation", the immune system may mount an anti-idiotypic response, unless the antibody is compatible with the host idiotype.

Additionally, there are many other foreign, ie non-human, substances administered to individuals for a variety of purposes, including therapy, and for which "humanising" techniques are not available. One of numerous examples well known to those skilled in the art is the "clot-busting" drug streptokinase administered to heart-attack patients. This enzyme is bacterial in origin and an immune response is mounted against it by recipient individuals.

The present invention additionally provides a way of inhibiting the immune response to an immunogen.

The present invention in its various aspects is founded on the surprising discovery that coupling of the Complement C3 fragment C3d (a ligand for CD21 (CR2)) to immunogen of interest enables modulation of the immune response to the immunogen. The modulation may be an increase or a decrease in the level of antibody response to immunogen administration. Completely unexpectedly, it has been found that the immune response may be enhanced by coupling a plurality of C3d molecules, to the immunogen and reduced by coupling of one C3d molecule to the immunogen. In view of this, the present invention in various aspects relates to modulation of an immune response by associating an antigen with a ligand for CD21 or, since CD21 associates with CD19 on the surface of B cells, a ligand for CD19.

Thus, according to the present invention there is provided a method of altering the immunogenicity of an immunogen, the method comprising forming a composition comprising the immunogen in association with (or "coupled to") a ligand for CD21 (CR2) or CD19. In a preferred embodiment the method comprises coupling one or more C3d molecules to the immunogen. If the C3d coupled is monomeric, the immunogenicity of the immunogen is reduced. If the C3d coupled is multimeric, eg dimeric, the immunogenicity of the immunogen is increased. With increased or decreased immunogenicity, the immune response of an individual who receives the immunogen will be enhanced or reduced, respectively. The level of immune response may be measured, for example, with reference to antibody levels.

The association of antigen and ligand may be such that there is modulation of a response in a B cell through two receptors on the B cell; a membrane immunoglobulin (mIg) specific for the antigen and a CD21/CD19 complex. Preferably, a response in a B cell is stimulated, but in certain circumstances, e.g. as discussed, a response in a B cell may be inhibited. Experimental assays for assessing ability to modulate B cell responses through mIg and the CD21/CD19 complex are described herein. For example, an increase in intracellular calcium concentration upon stimulation of antigen-specific B cells using the invention (as compared with stimulation with antigen alone) may be used as an indicator that the composition stimulates B cells through mIg and CD21/CD19.

The experimental work described herein includes evidence of T-cell involvement in the immune response. B-cell responses to protein antigens are T-cell-dependent. Furthermore, T-cell-independent responses do not develop memory: memory is demonstrated herein. Also, isotype switching is characteristic of T-cell-dependent B-cell responses.

In a second aspect, the invention provides a composition comprising an antigen/immunogen in association with (or "coupled to") a ligand for CD21(CR2) or CD19. Such a composition may comprise a molecule (conjugate) comprising an antigen or immunogen coupled to one or more C3d molecules. If a plurality of C3d molecules are linked to the antigen it may be preferred to use 2 or 3, as exemplified herein. Since the experimental evidence described below indicates an increase in effect with increasing number of C3d molecules, it may be preferred, depending on circumstances, to use a greater number, e.g. 4 or 5 or more.

Since a preferred way of coupling to C3d is by a peptide bond, the conjugate may be a contiguous polypeptide, ie a fusion protein. In a fusion protein according to the present invention, different peptides or polypeptides are linked in frame to each other to form a contiguous polypeptide. Thus a first portion of the fusion protein comprises an antigen or immunogen and a second portion of the fusion protein, either N-terminal or C-terminal to the first portion, comprises a CD21 or CD19 ligand. It is preferred that the antigen is linked to the amino terminus of the C3d molecule or repeat. When the CD21 or CD19 ligand is an antibody fragment such as a single chain Fv molecule (scFv), it is preferred that the fusion is at the C-terminal end of the scFv molecule to avoid damaging its binding capability.

A flexible linker sequence (e.g. a polyglycine/polyserine-containing sequence such as $[Gly_4Ser]_2$ (Huston et al (1991) *Meth. Enzymol* 203: 46–88) may be inserted into the fusion protein between the antigen and ligand. Also, the fusion protein may be constructed to contain an "epitope tag", which allows the fusion protein to bind an antibody (e.g. monoclonal antibody) for example for labelling or purification purposes. An example of an epitope tag is a Glu-Glu-Phe tripeptide which is recognised by the monoclonal antibody YL1/2.

Conveniently where the immunogen is a peptide or polypeptide, nucleic acid encoding the immunogen may be fused to nucleic acid encoding the ligand, such as C3d, either a single C3d molecule or a repeat.

Accordingly, a further aspect of the invention provides a nucleic acid construct comprising a sequence of nucleotides encoding a ligand of CD21 or CD19 (e.g. C3d) fused to a sequence of nucleotides encoding an antigen/immunogen of interest. Preferably, the nucleic acid construct is an expression vector comprising a suitable promoter for expression of the fusion.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, COS cells, HeLa cells, baby hamster kidney cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, eds. Ausubel et al., John Wiley & Sons, 1992. Transformation procedures depend on the host used, but are well known.

A further aspect of the invention provides a host cell comprising a nucleic acid construct as disclosed above. A still further aspect provides a method of making a polypeptide fusion comprising a ligand of CD21 or Cd19, preferably one or more C3d molecules, and another (heterologous) polypeptide or peptide, the method comprising culturing host cells comprising a nucleic acid construct which comprises a sequence of nucleotides encoding the polypeptide fusion under conditions for expression of the polypeptide fusion. Expression may be followed by isolation of the polypeptide fusion from the cells or, if secreted by the cells, from the culture medium.

Nucleic acid for use according to the invention may be DNA or RNA, and may be single-stranded or double-stranded, cDNA, genomic DNA or wholly or partially synthetic. Double-stranded DNA is preferred.

The nucleotide sequence and predicted amino acid sequence of mouse C3d are disclosed in Domdey et al. (1982) *PNAS USA* 79: 7619–7623 and Fey et al (1983) *Ann. N.Y. Acad. Sci.* 421: 307–312). The nucleotide sequence and predicted-amino acid sequence for human C3d are disclosed in de Bruijn and Fey (1985) *PNAS USA* 82: 708–712. Nucleic acid encoding C3d from other species may be isolated using the human or mouse sequence information to prepare one or more probes for use in standard hybridisation methods. When C3d is to be employed in the invention and administered to a subject, the C3d may be matched to the species to be immunised (e.g. mouse C3d to be used in mouse, human C3d in human and so on). However, experimental evidence is included herein demonstrating species cross-reactivity, at least between mouse and human (e.g. mouse C3d binds to CD21 on human cells, such as human Raji B lymphoblastoid cells), so species matching of C3d and subject may not be essential, even if preferred.

In an embodiment alternative to coupling of antigen/immunogen and CD21/CD19 ligand by expression as a fusion protein, chemical cross-linking may be employed. "Chemically cross-linked" refers to covalent linkage through use of a chemical cross-linking agent. A chemical cross-linking agent is chosen that reacts with functional groups on the antigen and ligand (e.g. amino acid side chains or the amino- or carboxy-terminus of a peptide chain) such that upon reaction with the cross-linking agent the antigen and ligand become covalently linked. Moreoever, the cross-linking agent may contain a spacer molecule that serves to position properly the antigen and ligand such that they can interact with mIg and the CD21/CD19 complex, respectively.

A wide variety of bifunctional or polyfunctional cross-linking reagents, both homo- and heterofunctional, are known in the art and are commercially available (e.g. Pierce Chemical Co., Rockford, Ill.). Such cross-linking reagents may be reacted with the antigen and ligand by standard methods (e.g. according to the manufacturers instructions). Following cross-linkage, the antigen-ligand complex may be purified from unreacted antigen and ligand by standard methods (e.g., chromatography, SDS-PAGE and the like). The efficacy of chemically cross-linked compositions in stimulating intracellular signals in B cells (e.g. increased intracellular calcium concentrations) and/or modulating immune responses can be evaluated using assays, e.g. as described herein.

Ligands for use in a chemically-crosslinked composition are as disclosed. A preferred ligand is one or more C3d molecules. C3d for use in a chemically-crosslinked composition may be recombinant C3d (e.g. prepared by expression from encoding nucleic acid) or purified, natural C3d. For example, C3 can be purified from plasma (e.g. human plasma) and C3d can be prepared therefrom by digestion as described in Lambris, J. D. et al. (1980) *J. Exp. Med.* 152:1625.

In another embodiment, antigen and ligand may be co-expressed (i.e. both present) on a surface of a carrier structure. Preferably, the antigen and the ligand are co-expressed on the surface of the carrier structure such that, upon contact with a B cell, the antigen can interact with membrane immunoglobulins (mIg) specific for the antigen on the surface of the B cell and the ligand can interact with the CD21/CD19 complex on the surface of the B cell.

The carrier structure used for co-expression of the antigen and the ligand may be a liposome (or similar vesicle-type structures that can carry material on their surface, such as microspheres, polyacryl starch microparticles, microcapsules and the like). Antigens and ligands can be covalently attached to the surface of a liposome or other carrier vesicles by standard methods. For review, see Jones, M. N. (1995) *Adv. Colloid. Interface Sci.* 54:93–128. See also e.g., Heath, T. D. et al. (1980) *Biochim. Biophys. Acta* 599:42–62; Heath, T. D. and Martin, F. J. (1986) *Chem. Phys. Lipids* 40:347–358; Hutchinson, F. J., et al. (1989) *Biochim. Biophys. Acta* 978:17–24; Therien, H. M. et al. (1991) *Cell. Immunol.* 136:402–413; Freide, M., et al. (1993) *Anal. Biochem.* 211:117–122. For stimulation of immune responses to the antigen, use of a liposome or a polyacryl starch microparticle as a carrier structure for the antigen and the ligand may have the additional benefit that the liposome or microparticle itself may have adjuvant activity (or can carry an additional adjuvant, such as the monophosphoryl adjuvant lipid A). For a review, see Alving, C. R. (1995) *Immunol. Rev.* 145:5–31. See also e.g. Raphael, L. and Tom, B. H. (1984) *Clin. Exp. Immunol.* 55:1–13; Artursson, P., et al. (1986) *J. Pharm. Sci.* 75:697–701; Degling, L. and Stjaernkvist, P. (1995) *Vaccine* 13:629–636; Lachman, L. B., et al. (1995) *AIDS Res. Hum. Retrovirus.* 11:921–932. A preferred liposome formulation for stimulating immune responses may comprise an alum-adsorbed liposome containing lipid A and having an antigen and a CD21 or CD19 ligand bound to the surface of the liposome.

The carrier structure may be a cell. For example, a cell can be transfected with recombinant expression vectors encoding membrane-bound forms of the antigen and the ligand such that expression of the vectors in the cell leads to cell-surface expression of the antigen and the ligand. Surface expression of the antigen can be achieved, for example, by linking a DNA fragment encoding a signal sequence to the 5' end of a DNA encoding the antigen (if the antigen does not itself contain a signal sequence) and linking a DNA fragment encoding a transmembrane domain to the 3' end of the DNA encoding the antigen (if the antigen itself does not contain a transmembrane domain), using standard recombinant DNA techniques. The ligand may be modified similarly to achieve cell-surface expression of the ligand. A high level of expression of the antigen and the ligand may be necessary to achieve cross-linking of both mIg and CD21/CD19 on B cells. Accordingly, recombinant expression vectors utilizing strong regulatory elements (e.g. one or more strong enhancers) may be preferred for expression of the antigen and the ligand on surface of the carrier cell.

The carrier structure may be any vaccine or biological particle for administration, for example in the membrane or on the surface of a virus, on HBsAg particles and so on. Coexpression of the antigen/immunogen and ligand for CD21 or CD19 may follow incorporation of appropriate nucleic acid into the viral genome.

The carrier structure may be a solid support, such as a bead (e.g. agarose, sepharose, polystyrene and the like) or a plate. An antigen and a CD21 or CD19 ligand can be attached to a solid support by standard techniques. For example, chemical cross-linking agents such as those described herein may be used to covalently attach the antigen and the ligand to the solid support.

Administration of a composition according to the invention, such as a $(C3d)_n$-antigen conjugate, modulates the immune response of the recipient individual. Accordingly, a further aspect of the present invention provides a method of modulating the immune response of an individual to an antigen/immunogen of interest, the method comprising administration of a composition comprising an antigen/immunogen associated with a ligand of CD21 or CD19, such as a molecule comprising the antigen/immunogen coupled to one or more C3d molecules, as disclosed. Enhancement, augmentation, or increase of the immune response may be achieved by coupling a plurality of C3d molecules to the immunogen. Inhibition, reduction or decrease of the immune response may be achieved by the coupling of one C3d molecule.

The administration may be for a prophylactic purpose ("vaccination", e.g. anti-microbial) or therapeutic, e.g in immunotherapy (e.g. anti-microbial or anti-tumour). Vaccination may be used to confer on a subject protective immunity to an antigen.

Instead of administering the conjugate in the case of a peptide or polypeptide DNA encoding a fusion may be administered, in accordance with known techniques (4, 5, 6). This may be particularly advantageous for stimulation of CTL responses (see below), because the fusion is expressed intracellularly in cells of the subject, which is known to promote antigen presentation by MHC class I molecules that stimulate $CD8^+$ T cells, such as CTL. DNA may be administered-for example by direct intramuscular injection of DNA or administration of a DNA-cationic lipid formulation (see e.g. Cohen, J. (1993) *Science* 259: 1691–1692; Yankauekas, M. A., et al. (1993) *DNA Cell Biol.* 12: 771–776; Boots, A. M., et al. (1992) *Vaccine* 10: 119–124; Conry, R. M., et al. (1994) *Cancer Res.* 54: 1164–1168; Montgomery, D. L., et al. (1993) *DNA Cell. Biol.* 12: 777–783; Wang, B., et al. (1993) *DNA Cell Biol.* 12: 799–805; San, H., et al. (1993) *Hum. Gene Ther.* 4: 781–788; Felgner, J. H., et al. (1994) *J. Biol. Chem.* 269:2550–2561; Duzgunes, N. and Felgner, J. H. (1993) *Methods Enzymol.* 221:303–306; Jiao, S., et al. (1992) *Exp. Neurol.* 115:400–413).

Applications of such administration are discussed above, including raising of antibodies to the immunogen. In a further aspect the invention for instance provides a method of raising an antibody response (obtaining antibodies) to an antigen/immunogen of interest which comprises administration to a mammal of the antigen/immunogen in association with a ligand of CD21 or CD19, e.g. coupled to a plurality of C3d molecules, as disclosed. Generally the mammal may be eg human, mouse, rat, rabbit, horse, goat, sheep or monkey. The purpose of administration may be therapeutic or may be to raise antibodies for later use/manipulation, eg using recombinant techniques such as monoclonal antibody technology and/or bacteriophage display (see eg WO92/01047). Isolation of antibodies and/or antibody-producing cells from the mammal may be accompanied by a step of sacrificing the animal.

In accordance with the present invention antibody production in vitro, e.g. in culture, may be stimulated. For example, B cells specific for an antigen of interest may be cultured with a stimulatory composition of the invention to stimulate production by the B cells of antibody for the antigen of interest. The antibodies produced may be isolated from the culture medium, e.g. by virtue of their binding capability for the antigen.

The administration may be made in order to modulate (preferably induce or stimulate) a T-cell response to the immunogen, for example in anti-microbial (including anti-viral) and anti-cancer immunotherapy. Evidence of T-cell involvement in an immune response to administration of a composition in accordance with the present invention is discussed above. Stimulation of T-helper cells, providing help for B cell activation, may promote development of cytotoxic T cells (CTL). Thus, if an epitope of a tumour marker is coupled to a CD21 or CD19 ligand, such as a plurality of C3d molecules, and administered to an individual who has a tumour expressing the epitope, the enhanced immune response to the epitope resulting from the administration may have a therapeutically beneficial effect on the tumour. Also, because CTL secrete IFN-γ, which gives a TH1 bias, the administration may be used for allergy.

In a further aspect, the present invention provides a pharmaceutical composition which comprises an antigen/immunogen in association with a ligand of CD21 or CD21, such as a $(C3d)_n$-immunogen conjugate, as disclosed.

Pharmaceutical compositions according to the present invention may comprise, in addition to the antigen/immunogen in association with a CD21 or CD19 ligand, e.g. $(C3d)_n$-immunogen conjugate, a pharmaceutically acceptable excipient, carrier, vehicle, buffer, stabiliser or other materials well known to those skilled in the art. Such materials should be non-toxic and should not interfere with the efficacy of the active ingredient. The precise nature of the carrier or other material will depend on the route of administration, which will preferably be cutaneous, subcutaneous or intravenous injection, especially subcutaneous.

For parental, intravenous, cutaneous or subcutaneous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, anti-oxidants and/or other additives may be included, as required. Sub-cutaneous injection may be preferred route of administration.

A pharmaceutical composition in accordance with the present invention may comprise one or more additional active ingredients. For example, the composition may contain an additional agent that has immunomodulatory properties, such as a cytokine or (additional) adjuvant.

Another aspect of the present invention provides the use of an antigen/immunogen in association with a CD21 or CD19 ligand, e.g. $(C3d)_n$-immunogen, (as disclosed) in the manufacture of a composition or medicament for administration to an individual to modulate the immune response of the individual to the immunogen. The purpose of administration may be to obtain antibodies, as discussed.

The present invention is applicable to a wide variety of antigens. In a preferred embodiment, the antigen is proteinaceous, protein, polypeptide or peptide. In another embodiment the antigen is DNA. The antigen may be lipid. It may be a carbohydrate. Preferred antigens include those from a pathogen (e.g. virus, bacterium, parasite) and tumours (especially tumour-associated antigens or "tumour markers"). Other preferred antigens are autoantigens. Examples of tumour-associated antigens include carcinoembryonic antigen (CEA), prostate-specific antigen (PSA), muc-1 (Agrawal et al. (1995) *Cancer Res.* 55: 2257–2261), MART-1 (Kawakami et al (1994) *J. Exp. Med.* 180:347–352) and gp100 (Adema et al (1994) *J. Biol Chem.* 269: 20126–20133). Examples of viral antigens include herpes simplex virus-I proteins such as gB, gC, gD, g EW, gG, gH, gI, gK, gL, Vmw65, ICP0 and Icp4, haemagglutinin of a myxovirus (e.g. influenza, mumps or measles) and gp120 of human immunodeficiency virus.

Note that "C3d" as referred to herein may be a mutant, derivative or fragment thereof (e.g. by way of addition, insertion, substitution or deletion of one or more amino acids) provided ability to augment or reduce immunogenicity/an immune response is retained. For instance, a portion of C3d that retains the ability to bind CD21 and stimulate B cells through the CC 21/CD19 complex may be employed. A CD21-binding site on C3 has been mapped to amino acid residues 1205–1214 of the C3 sequence (Lambris et al (1985) *PNAS USA* 82:4235) and synthetic C3 peptides comprising amino acid residues 1201–1214 or 1187–1214 have been shown to bind CD21 (Servis and Lambris (1989) *J. Immunol.* 142:2207). Similar peptides or other CD21-binding C3 peptides may be employed in the present invention.

C3d may be modified such that it does not contain an internal thioester. For example, $Cys_{1028}$ of C3d, which is involved in formation of the thioester, may be mutated to Ser by standard methods.

Instead of C3d, other CD21 or CD19 ligands may be employed, such as one or more iC3b molecules, one or more C3dg molecules, an antibody or antigen-binding fragment or portion thereof that binds specifically to CD21 or CD19. Compared with C3d, the iC3b and C3dg subfragments are likely to be more susceptible to tryptic digestion, so C3d is preferred for use in vivo as compared with iC3d or C3dg. However, modified forms of iC3d or C3dg in which tryptic digestion site or sites have been mutated such that the fragments are more resistant to proteolytic digestion may be more suitable for use in vivo.

If an antibody or fragment or derivative thereof is employed it must be coupled (e.g. fused) to the antigen or immunogen in a way which retains the ability to bind CD21 or CD19. This may be by fusion with a constant region of a heavy or light chain of an antibody. Fusion at the C-terminus of single chain Fv (scFv) antibody fragments has been shown not to interfere with binding ability of the scFv's. As antibodies can be modified in a number of ways, the term "antibody" should be construed as covering any specific binding substance having an binding domain with the required specificity. Thus, this term covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544–546 (1989))

which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423–426, 1988; Huston et al, PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444–6448, 1993).

Antibodies to CD21 have been described and are available in the art (e.g. OKB7, Ortho Pharmaceuticals, Raritan, N.J., USA; and HB-5, American Type Culture Collection, Rockville, Md., USA, No HB 135). Antibodies to CD19 are also available in the art (e.g. Carter et al (1991) *J. Immunol* 147: 3663–3671; and Holder et al (1992) *Eur. J. Immunol.* 22: 2725–2728).

Antibodies which are specific for a target of interest may be obtained using techniques which are standard in the art. Methods of producing antibodies include immunising a mammal (eg mouse, rat, rabbit, horse, goat, sheep or monkey) with the protein or a fragment thereof, or a cell or virus which expresses the protein or fragment. Immunisation with DNA encoding a target polypeptide is also possible. Antibodies may be obtained from immunised animals using any of a variety of techniques known in the art, and screened, preferably using binding of antibody to antigen of interest. For instance, Western blotting techniques or immunoprecipitation may be used (Armitage et al, 1992, Nature 357: 80–82).

As an alternative or supplement to immunising a mammal, an antibody may be obtained from a recombinantly produced library of expressed immunoglobulin variable domains, eg using lambda bacteriophage or filamentous bacteriophage which display functional immunoglobulin binding domains on their surfaces; for instance see WO92/01047. The library may be naive, that is constructed from sequences obtained from an organism which has not been immunised with the target, or may be one constructed using sequences obtained from an organism which has been exposed to the antigen of interest (or a fragment thereof).

It is possible to take antibodies and use the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma producing a monoclonal antibody may be subject to genetic mutation or other changes, which may or may not alter the binding specificity of antibodies produced.

It may be desirable to "humanise" non-human (eg murine) antibodies to provide antibodies having the antigen binding properties of the non-human antibody, while minimising the immunogenic response of the antibodies, eg when they are used in human therapy. Thus, humanised antibodies comprise framework regions derived from human immunoglobulins (acceptor antibody) in which residues from one or more complementary determining regions (CDR's) are replaced by residues from CDR's of a non-human species (donor antibody) such as mouse, rat or rabbit antibody having the desired properties, eg specificity, affinity or capacity. Some of the framework residues of the human antibody may also be replaced by corresponding non-human residues, or by residues not present in either donor or acceptor antibodies. These modifications are made to the further refine and optimise the properties of the antibody.

So-called "phage display" may also be used in humanising antibodies; see e.g. WO93/06213.

The present invention is not intended to cover naturally-occuring complexes of antigen/immunogen and a C3 fragment that is produced when the alternative pathway of complement is activated and C3 fragments are deposited on antigen via reaction through the internal thioester bond of the C3. Accordingly, in compositions according to the present invention, association of antigen/immunogen with a ligand for CD21 (CR2) or CD19 has the proviso that the antigen/immunogen is not associated with a complement C3 fragment through an ester bond derived from the internal thioester of the complement C3 fragment. (The cysteine residue which forms the thioester residue may be employed in chemical cross-linking via a disulphide bridge, but this is not an ester bond.)

Further aspects and embodiments of the present invention will be apparent to those skilled in the art.

Embodiments of the present invention will now be illustrated by way of example and not limitation with reference to the figures. All documents mentioned herein are incorporated by reference.

The results show the mean of 4 (700 pmol HEL-C3d) or 5 (all other groups) animals+1 s.d.

Figure 1:
FIG. 1 shows a schematic representation of the structure of hen egg lysozyme—C3d recombinant proteins. Model of HEL, HEL-C3d, HEL-C3d$_2$ and HEL-C3d$_3$ proteins showing the joining sequences between the domains of the cassette (SEQ ID NOS: 15 and 16). Abbreviations for the amino acid residues are as follows: C, Cys; E, Glu; F, Phe; G, Gly; and S, Ser. Ligation of BamHI and BglII restriction sites generate the Gly Ser linker (14) which flanks the HEL, C3d, and [Gly$_4$Ser]$_2$ sequences. Also indicated is the mutation of Cys$_{1028}$ to Ser. Each construct terminates with the Glu Glu Phe tripeptide which is recognized by the monoclonal antibody YL ½.
Figure 1:
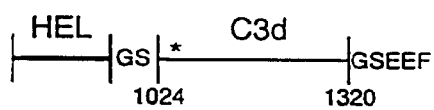
Figure 1:
Figure 1:
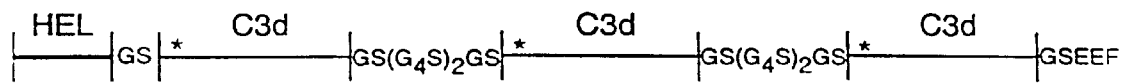
Figure 2:
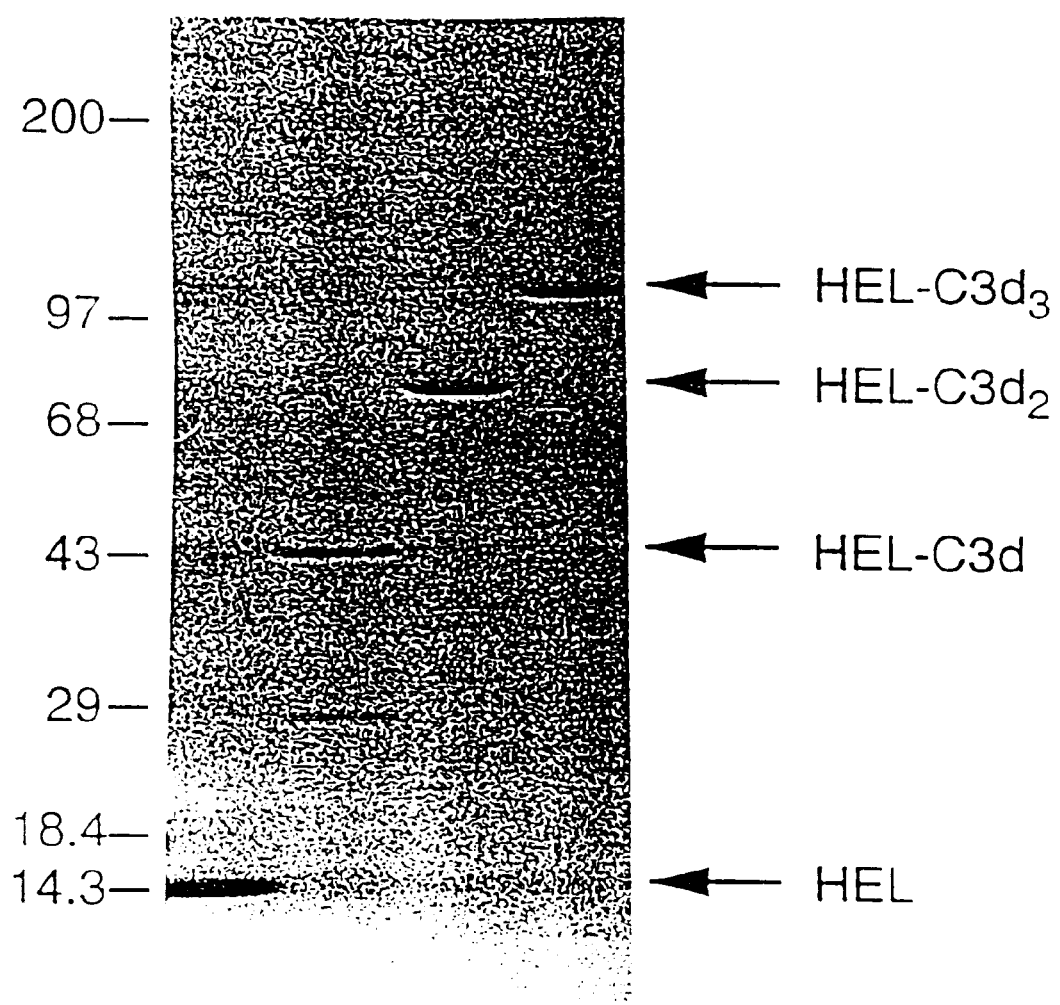
FIG. 2 shows a 5–20% SDS-polyacrylamide gel, run under reducing conditions of purified, hen egg lysozyme—C3d recombinant proteins. Molecular size standards are shown on the left margin in kilodaltons.
Figure 3:
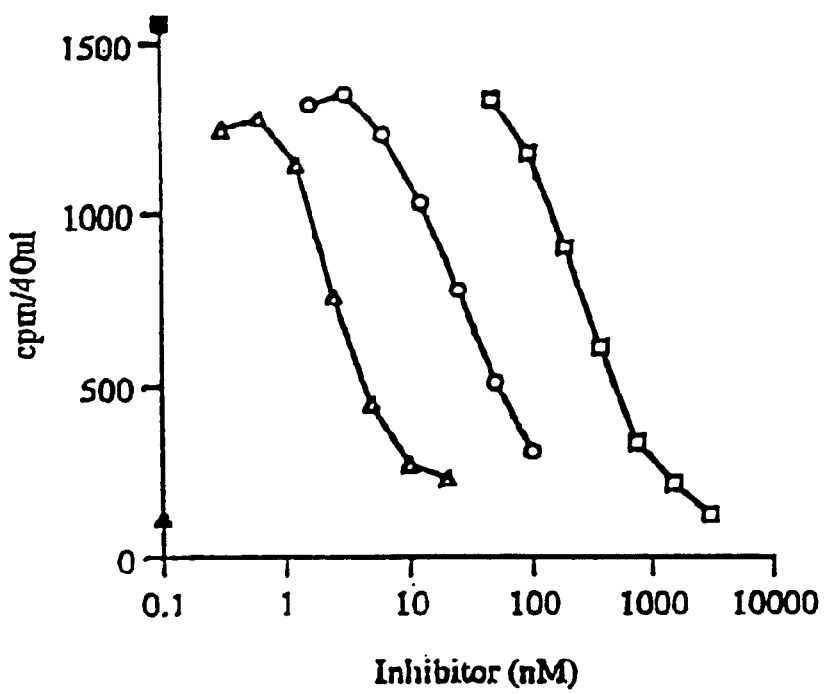
FIG. 3 illustrates inhibition of [$^{125}$I]HEL-C3d$_2$ binding of Raji cells. (□—HEL.C3d; ○—HEL.C3d$_2$; △—HEL.C3d$_3$; ■ IgG1; ● no inhibitor; ▲CR2)
Figure 4:
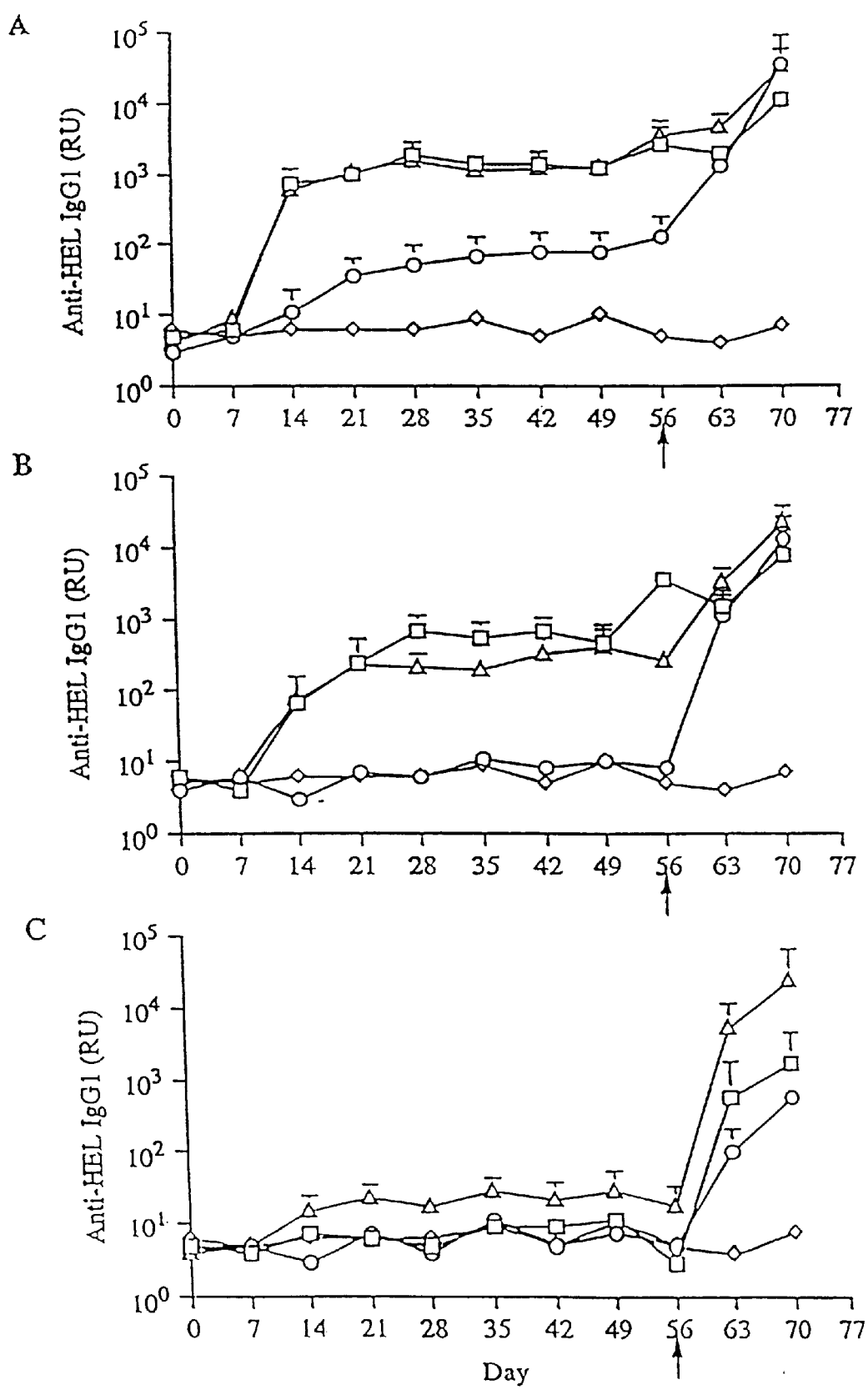
FIGS. 4A to 4C show IgG1 response to recombinant antigen in CFA. HEL (squares), HEL-C3d (circles), and HEL-C3d$_2$ (triangles) recombinant antigen was diluted to a final concentration of 500 pmol (panel A), 50 pmol (panel B), or 5 pmol (panel C) in 0.05 ml PBS. The antigens were emulsified with equal volumes of complete Freund's adjuvant, and 0.1 ml of the emulsion was injected intraperitoneally into groups 4–6 week old male CBA/Ca mice (Harlan U.K.). Control mice received CFA emulsified with PBS alone (diamonds). Mice were bled successively at 7 day intervals. All groups of animals received 50 pmol HEL in 0.5 ml PBS emulsified with an equal volume of incomplete Freund's adjuvant at day 56 (arrow). HEL specific response was determined by elisa as described. Results show means of groups of 5 animals+1 s.d.
Figure 5:
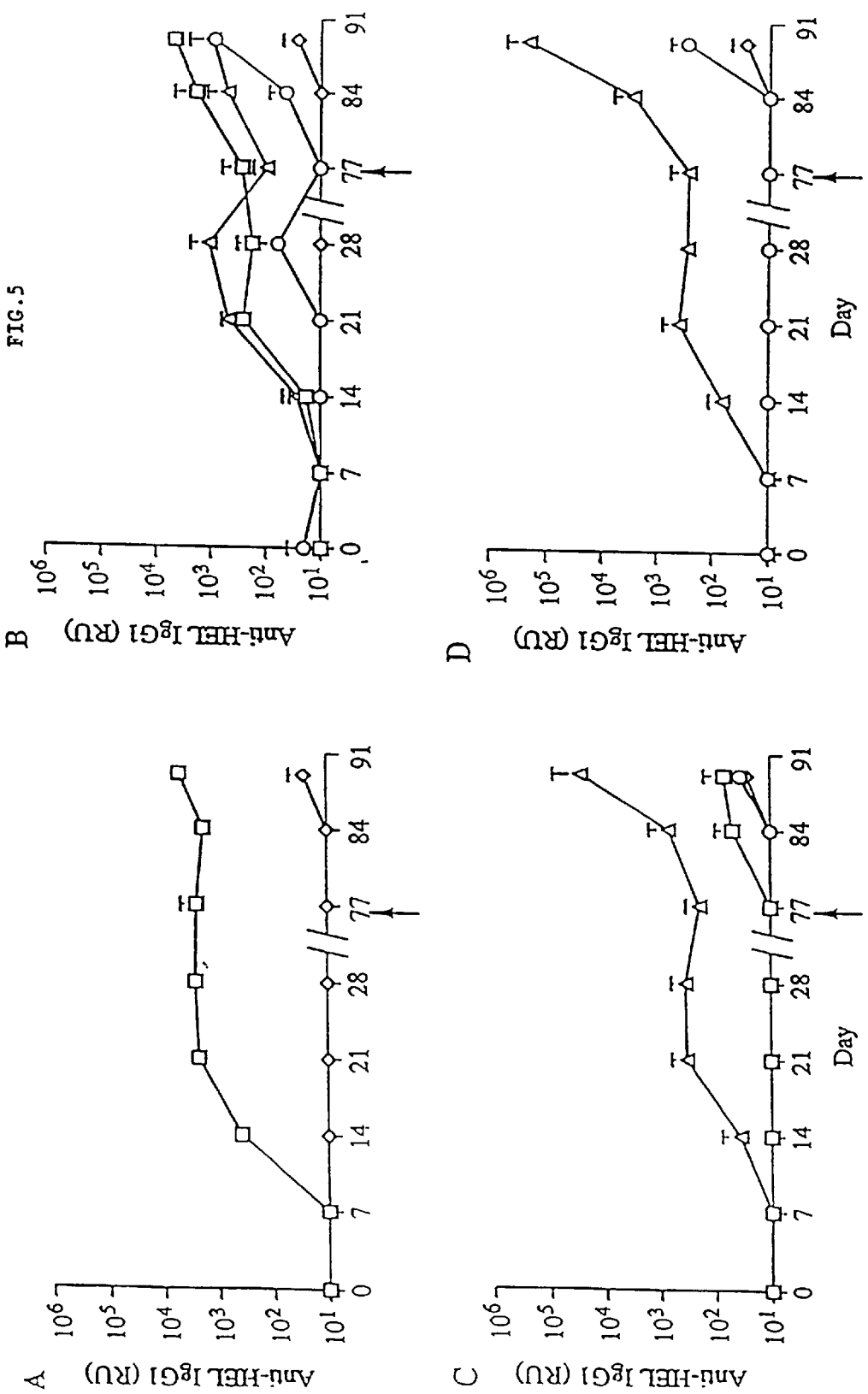
FIGS. 5A to 5D show IgG1 response to subcutaneous recombinant antigen in saline. HEL (squares), HEL-C3d (circles), and HEL-C3d$_2$ (triangles) antigens were diluted in PBS to a final concentration of 7000 pmol (panel A), 700 pmol (panel B), or 70 pmol (panel C), or 7 pmol (panel D) in 0.1 ml. The antigens were injected subcutaneously in the rear right flank of 4–6 weeks old male CBA/c mice. Control mice received PBS alone (diamonds). Mice were bled successively at 7 day intervals. All groups received 50 pmol HEL in 0.05 ml PBS emulsified with an equal volume of incomplete Freund's adjuvant on day 77 (arrow). HEL specific response was determined by limiting dilution alisa whereby the last twofold serial dilution with an $A_{570}>2$ s.d. above that of non-immune sera was taken as the specific titre.
Figure 6:
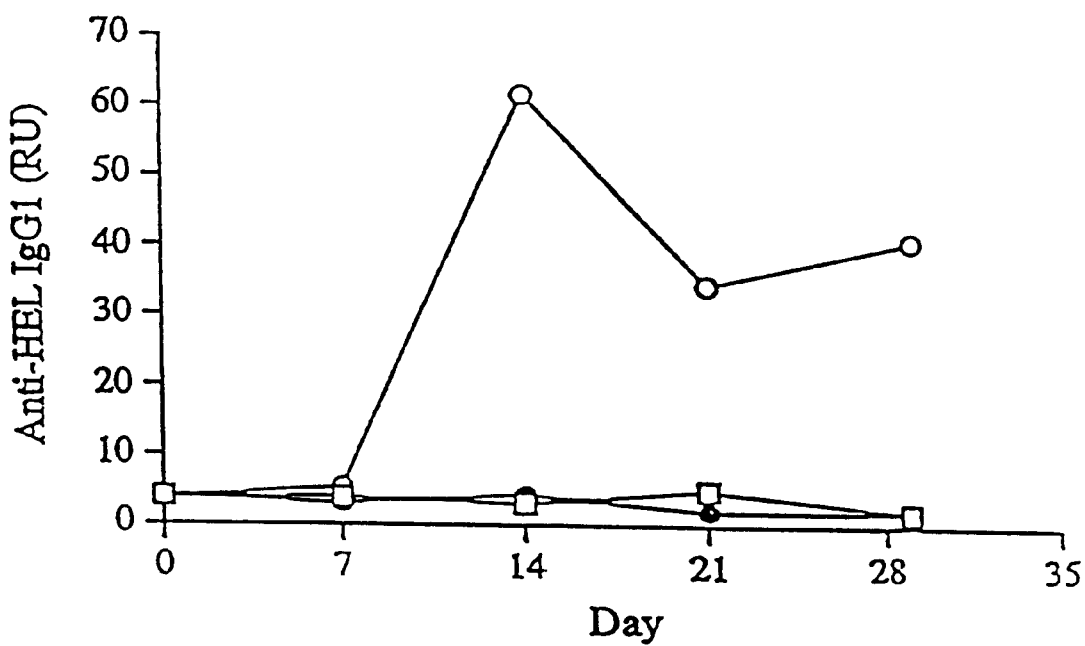

FIG. 6 shows suppression by 7G6 anti-CR2 of the response to $HEL-C3D_2$. 4–6 week old male CBA/c mice were injected intravenously with 0,2 mg 7G6 (closed circles) or control IgG2b (open squares and circles). 24 hours later, mice received 7 pmol $HEL-C3d_2$ in 0.1 ml PBS (circles) or 0.1 ml PBS (squares) subcutaneously in the rear right flank. The mice were bled successively at 7 day intervals and the HEL specific response was determined by elisa as described. Results show the mean of groups of three mice.

Figure 7:
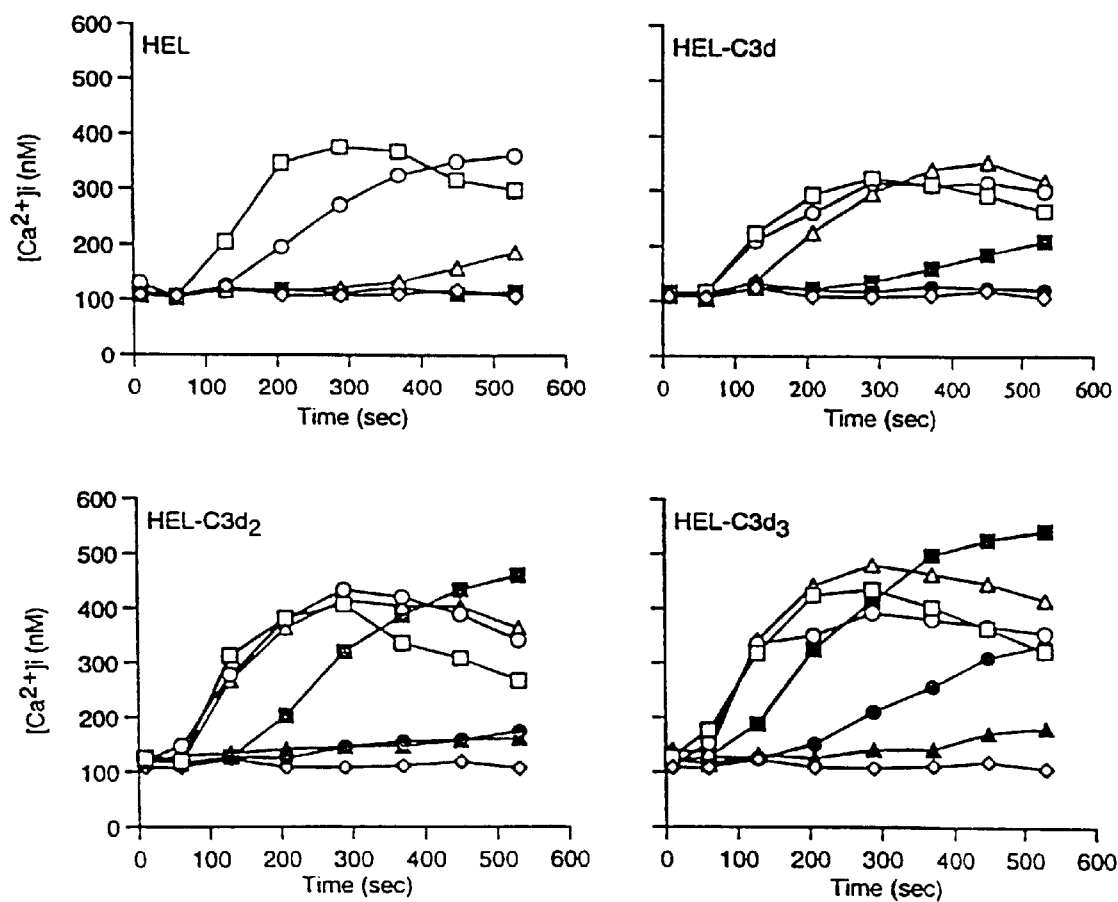

FIG. 7 shows stimulation by recombinant HEL and HEL-C3d1-3 of increases in $[Ca^{2+}]i$ in HEL-specific B cells. Splenic lymphocytes from transgenic mice with B cells expressing mIgM and mIgD specific for HEL were loaded with indo-1 and incubated with incremental concentrations of HEL, HEL-C3d, HEL-C3d2, and HEL-C3d3, respectively: 70 nM (□), 7 nM (○), 0.7 nM (△), 70 pM (■), 7 pM (●), 0.7 pM (▲), and buffer alone (◇). Changes in $[Ca^{2+}]i$ in B cells were monitored by flow cytometry.

Figure 8:
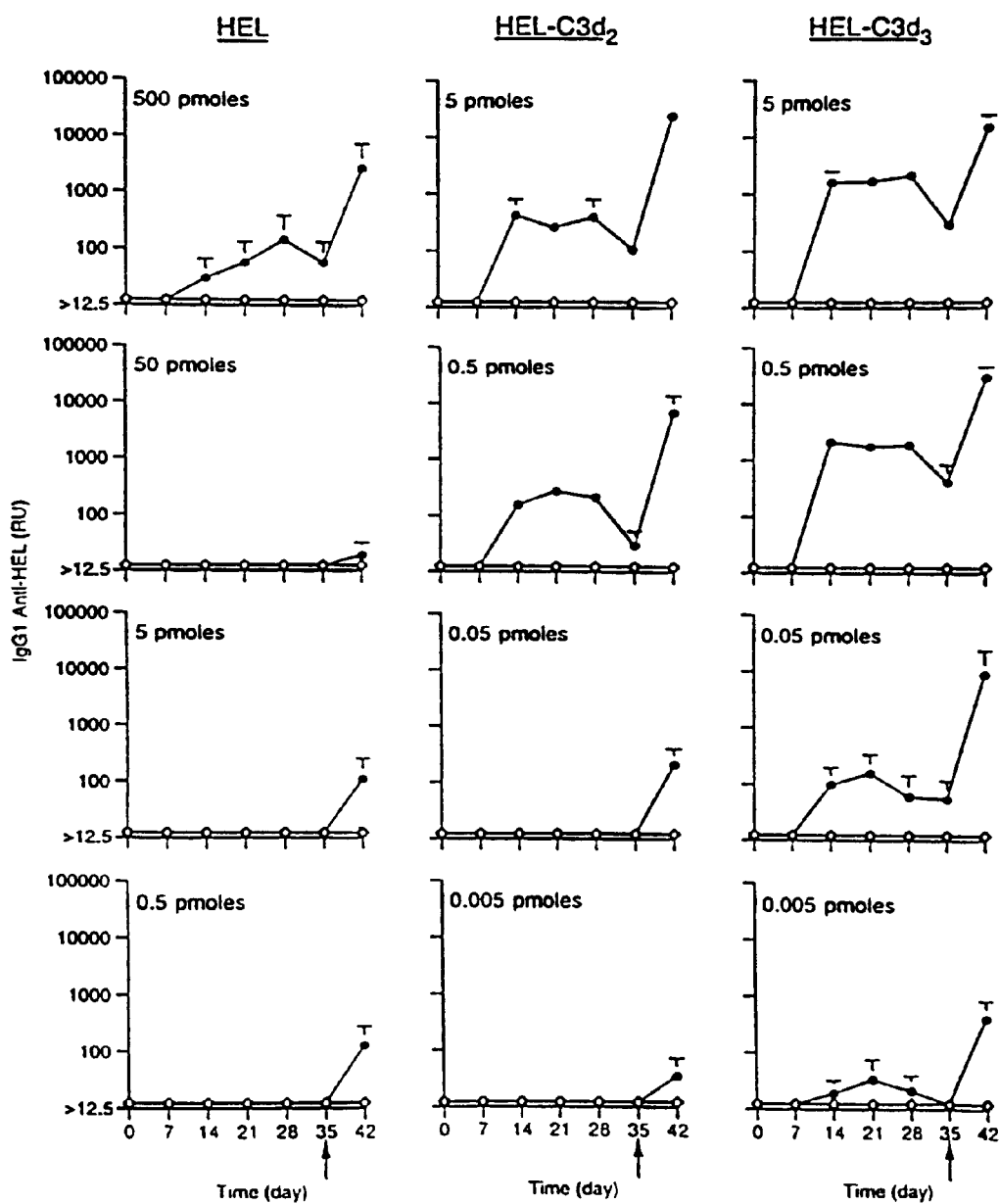

FIG. 8 shows the IgG1 anti-HEL response in mice immunized with recombinant HEL antigens subcutaneously in PBS. On day 0, groups of four mice were administered buffer alone (open symbols) or incremental amounts of HEL, HEL-C3d2, or HEL-C3d3 (closed symbols) subcutaneously in PBS. The mice were boosted on day 35 with 50 pmoles of HEL intraperitoneally in IFA, as indicated by the arrow. Sera were assayed by ELISA for HEL-specific IgG1 and titers are expressed as relative units (RU).

Figure 9:
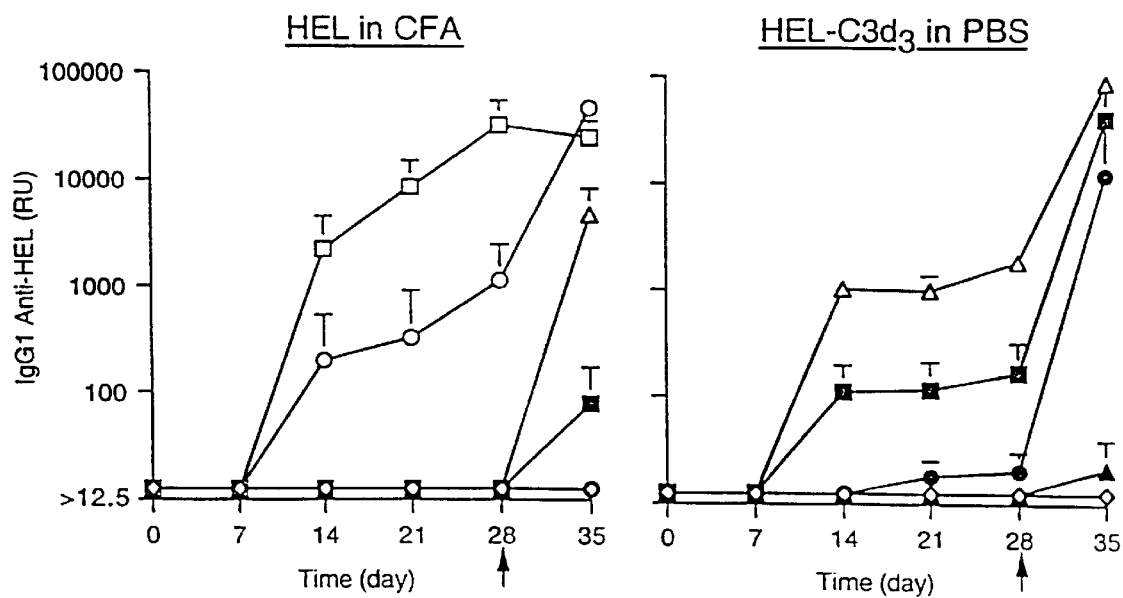

FIG. 9 shows comparison of the effects of CFA and C3d on the immunogenicity of HEL. On day 0, groups of five mice were administered 500 pmoles (□), 50 pmoles (○), 5 pmoles (△), 500 fmoles (■), 50 fmoles (●), or 5 fmoles (▲) of HEL, or buffer alone (◇) subcutaneously in CFA. Other groups of five mice were administered 5 pmoles (△), 500 fmoles (■), 50 fmoles (●), or 5 fmoles (▲) of HEL-C3d3, or buffer alone (◇) subcutaneously in PBS. All mice were boosted on day 28 with 50 pmoles of HEL in IFA as indicated by the arrow. The serum titers of HEL-specific IgG1 are expressed as RU.

Figure 10:
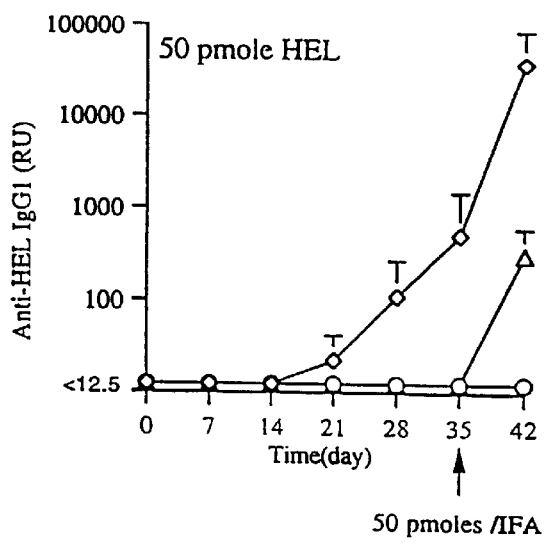
Figure 10:
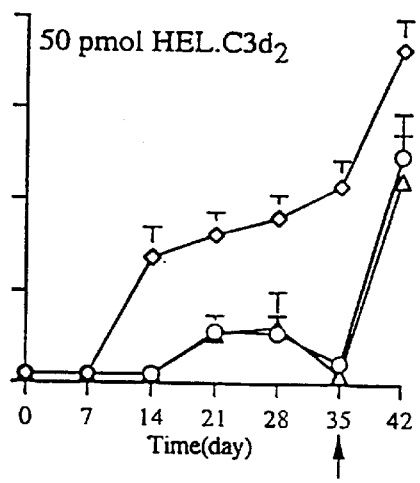
Figure 10:
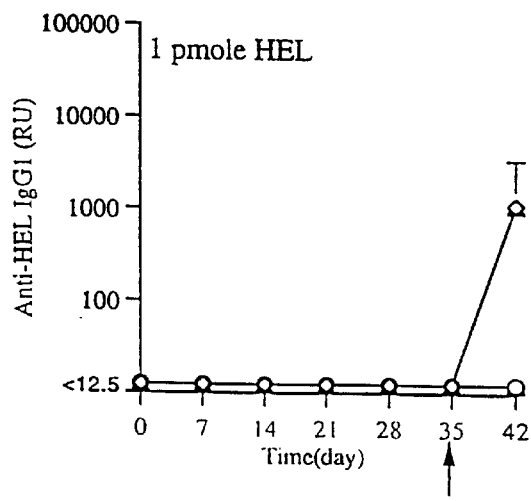
Figure 10:
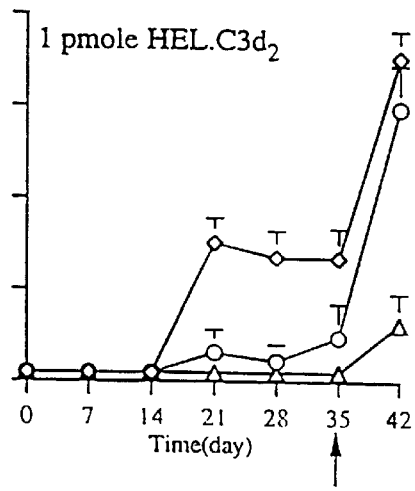

FIG. 10 shows comparison of the Ig G1 anti-HEL response in mice immunised with HEL or $HEL-C3d_2$ in PBS by various routes of administration. At day 0, groups of five mice were administered either 1 pmole or 50 pmoles of protein subcutaneously (diamonds), intramuscularly (circles) or intraperitoneally (triangles). The mice were boosted on day 35 with 50 pmoles of HEL in IFA intraperitoneally, as indicated by the arrow. Sera were assayed for HEL-specific IgG1 and titers are expressed as relative units (RU).

Construction and Expression of C3d/antigen Chimeras

For the DNA encoding C3d (7, 8), C3d was amplified by PCR using the EcoRI linearized pMLC3–7 cDNA clone as template, and 25 cycles of 2 min of denaturation, annealing and extension. The primers used were as follows:

5' C3d (SEQ ID NO 1):
5'-CACTCTAGACGCCGCAGATCTACCCCCGCAGG CTCTG GGGAACAGAACATGAT-3';

3' C3d (SEQ ID NO 2):
5'-CGCGGATCCACTGCTGGGGAGGTGGAAGGA-3'.

This and all subsequent PCR products were sequenced by the dideoxynucleotide chain termination method using the Sequence kit (U.S. Biochemical Corp.) XbaI and BglII sites were included in the 5' primer and BamHI in the 3' primer. Primers were designed to include the sequences between base pairs 3070 and 3960 of the complete murine C3 sequence. By including a G to C subsition in the 5' primer we were able to change the Cys codon at amino acid position 1028 to one encoding Ser, thereby mutating the critical Cys involved in thiolester bond formation. After amplification the fragments were digested with XbaI and BamHI and ligated into XbaI- and BamHI-digested pBS, to generate pBS.C3d.

For assembly of monomer constructs, an epitope tag recognised by the monoclonal antibody YL ½ (9, 10) and a stop codon was ligated onto the 3' end of C3d using oligonucleotides. pBS.C3d was digested with BamHI and EcoRI and ligated with the oligonucleotides encoding the YL½ epitope generating pBS.C3d.YL. The oligonucleotides were as follows:

5' YL½ (SEQ ID NO 3):
5'-GATCTGAAGAGTTCTGAGGATCCCGG-3';

3' YL½ (SEQ ID NO 4):
5'-AATTCCGGGATCCTCAGAACTCTTCA-3'.

For assembly of oligomeric C3d constructs, a [(Gly)$_4$Ser]$_2$ linker was amplified as part of a fusion sequence with hen egg white lysozyme by PCR using a PstI linearized pSVG-spcHEL template, and 25 cycles of 30 sec of denaturation, annealing, and extension. The primers were as follows:

5'GS (SEQ ID NO 5):
5'-GCCAGATCTGGTGGAGGTGGAAGT-3';

3'HEL (SEQ ID NO 6):
5'-CGGGATCCCAGCCGGCAGCCTCT-3'.

The fragments were cloned into pCRII (InVitrogen) and the 34 b.p. [(Gly)$_4$Ser]$_2$ linker subcloned by digestion with BamHI and BglII into BamHI digested pBS.C3d to generate pBS.C3d.GS. Ligation of the bamHI-BglII C3d.YL fragment from pBS.C3d.YL into BamHI digested pBS.C3d.GS generated pBS.C3d$_2$YL. Generation of pBS.C3d$_3$.YL was accomplished by repeating one round of BamHI and BglII digestion of pBS.C3d.GS and subcloning of the 937 b.p. C3d.GS fragment into BamHI digested pBS.C3d.GS. Subsequently, the pBS.C3d$_3$ construct was completed by BamHI and BglII digestion of pBS.C3d.YL and ligation of the 919 b.p. C3d.YL fragment into BamHI prepared pBS.C3d$_2$.

The dog pre-pro-insulin signal sequence (DPPISS) (11) was amplified from a PvuII linearized pGIR-477 (provided by K. Drickamer) template, using 25 cycles of 30 sec of denaturation, annealing and extension.

These primers were used:

5'DPPISS (SEQ ID NO 7):
5'-GCGAATTCCTAGCTTGC-3';

3'DPPISS (SEQ ID NO 8):
5'-GCGGATCCGGCTCGGGTGGGCGC-3'.

The fragments were digested with BamHI and EcoRI and ligated into BamHI-EcoRI digested pBS ("BLUESCRIPT")

to generate pBS.DPPISS. The eukaryotic expression vector pSG5 (Stratagene) was prepared by EcoRI- and BglII-digestion and subcloning of the EcoRI-BglIII DPPISS fragment from PBS.DPPISS generated pSG.SS. C3d containing fragments were subcloned from the pBS vectors by digesting pBS.C3d. YL, pBS.C3d$_2$.YL and pBS.C3d$_3$.YL with BamHI and BglII and ligating into BglII prepared pSG.SS to generate pSG.C3d.YL, pSG.C3d$_2$.YL and pSG.C3d$_3$.YL.

The antigen hen egg white lysozyme (HEL) (12) (C. Goodnow) was amplified from a PstI linearized template pDamian using 25 cycles of 30 sec of denaturation, annealing, and extension. The primers used were:

5'HEL (SEQ ID NO 9): 5'-GCAGATCTAAAGTCTTTGGACGA-3';

3'HEL (SEQ ID NO 10): 5'-CGGGATCCCAGCCGGCAGCCTCT-3'.

The fragments were cloned into PCRII. The HEL fragment was subcloned by digestion of pCRII.HEL with BamHI- and BglII- and ligation of the 404 bp HEL fragment into BglII- and BamHI-digested pSG.C3d.YL, pSG.C3d$_2$.YL and pSG.C3d$_3$.YL plasmids. The pCRII.HEL plasmid was also modified as described above to include the YL½ epitope and this 420 bp BglII-BamHI HEL.YL fragment was ligated into a BamHI- and BglII prepared pSG.SS vector giving pSG.HEL.YL. Subsequently, the pSG5 vector was modified to include the YL½ epitope directly by ligating into the BglII site of pSG5 the YL½ epitope. The oligonucleotides used were:

5'YL½ (SEQ ID NO 11): 5'-GATCTGAAGAGTTCTGAG-3';

3'YL½ (SEQ ID NO 12): 5'-GATCTGAAGAGTTCTGAG-3'.

For transient expression, pSG.HEL.C3d$_3$.YL was digested with EcoRI and XbaI. The 3468 bp HEL.C3d$_3$.YL fragment was blunt ended using the Klenow fragment of DNA Polymerase I and ligated into the A71d vector. A71d (gift of A. Venkitaraman), a eukaryotic expression vector, was prepared for ligation by digestion with BamHI and blunt ending of this site. Subsequent digestion with SmaI resulted in excision of a polyadenylation signal.

The plasmids pSG.HEL.YL, pSG.HEL.C3d.YL, and pSG.HEL.C3d$_2$.YL were co-transfected with pSV2-neo into L cells using the calcium phosphate procedure. The cells were selected with 0.8 mg/ml G418. Cells displayed G418 resistance were single cell cloned and those secreting high amounts of fusion protein were identified by elisa. Anti-HEL antibodies HyHEL-8 and biotinylated HyHEL-9 (13) were used in a capture elisa and detected by Avidin-horseradish peroxidase (BioRad). These transfectants were batch cultured in suspension or on Cytodex-1 microcarrier beads (Pharmacia), and the fusion antigens were purified from culture supernatants by affinity chromatography on YL½ antibody coupled at 10 mg/ml to 5 ml Sepharose 4B. The culture supernatants were passed over the affinity resin and washed with 10 column volumes each of Buffer 1 (50 mM Tris pH8.0, 150 mM NaCl, 0.1 mM EDTA) and then Buffer 1 supplemented with 0.2% NP40. The column was washed further with 20 column volumes of buffer 1 and fusion antigen then eluted with 50 mM TEA pH11.5, 150 mM NaCl, 0.1 mM EDTA. Antigen was neutralized, pooled and dialysed against PBS. The plasmid A71d.HEL.C3d$_3$.YL was transiently expressed in COS cells using the DEAE-dextram procedure and the fusion protein purified as described above. Purified HEL.C3d$_3$.YL and HEL.C3d$_2$.YL proteins were subsequently size fractionated on a high resolution Sephacryl S-200 column (Pharmacia) to remove contamination recombinant forms of the protein produced by the transfected cells.

Stimulation by Recombinant HEL and HEL-C3dl-3 of Increases in [Ca2+]i in HEL-specific B Cells Splenic lymphocytes from transgenic mice with B cells expressing mIgM and mIgD specific for HEL were loaded with indo-1. Splenocytes were stained with phycoerytherin conjugated rat anti-CD43. The CD43 positive cells were gated out and the cells incubated with incremental concentrations of HEL, HEL-C3d, HEL-C3d2, and HEL-C3d3, respectively. Changes in [Ca2+]i in B cells were monitored by flow cytometry. The results are shown in FIG. 7.

Coligating CD21 or CD19 to mIg with receptor-specific monoclonal antibodies lowers the threshold at which mIg stimulates an increase in intracellular free Ca2+ concentration ([Ca2+]i) (15, 16). B lymphocytes from mice expressing transgenes encoding mIgM and mIgD having a 2 nM Kd for HEL were loaded with indo-1, incubated with incremental concentrations of the recombinant HEL proteins, and assayed for changes in [Ca2+]i by flow cytometry (FIG. 7). HEL caused a dose-related increase in [Ca2+]i, with the threshold being 7 nM. The presence of 1, 2 and 3 copies of C3d on HEL lowered the threshold to 0.7 nM, 0.07 nM, and 0.007 nM, respectively, indicating that each C3d enhanced by 10-fold the ability of HEL to induce this cellular response. A saturating concentration of 7G6 anti-CD21 (17) caused the threshold for the response of HEL-C3d2 to revert to that of HEL. B cells from non-transgenic mice did not respond to HEL or HEL-C3d1–3. The changes in [Ca2+]i induced in non-transgenic B cells by antibody to mIgM was not altered by the presence of 7 nM HEL-C3d3. Incubation of transgenic B cells with 3 nM HEL and HEL-C3d3 for 10 min resulted in 51% and 47% saturation of the anti-HEL sites, respectively, as assessed by the subsequent binding of fluorescein-conjugated HEL, indicating that attachment of C3d to HEL did not improve binding to the transgenic B cells, presumably because of the high affinity of their antigen receptors for HEL. Therefore, the enhanced [Ca2+]i responses reflected augmented signaling through C3d-dependent recruitment of the CD21-CD19 complex.

Ability of the C3d Components of the Fusion Proteins to Bind CD21

The ability of the C3d components of the fusion proteins to bind to CD21 was determined by competitive binding assays using Raji B lymphoblastoid cells expressing CD21. Raji cells, 3–4×10$^7$ cells/ml, were incubated for 45 min. at 4° C. with 1 nM [$^{125}$I]HEL-C3d2 (specific activity 9.1×10$^5$ cpm/mg) and incremental concentrations of the HEL-C3d fusion proteins, 500 nM (CR2)2-IgG1 [T. Hebel, J. M. Ahearn, D. T. Fearon, Science 254, 102 (1991)], or IgG1 in PBS containing 0.1% bovine serum albumin. The cells were centrifuged through a dibutyl/diiso-octyl pthalate cushion and the amount of 125I bound to the cell pellet was determined. In two experiments, 50% inhibition of specific binding of [125I]HEL-C3d2 occurred with 185–225 nM HEL-C3d, 8–20 nM HEL-C3d2, and 1.5–2.2 nM HEL-C3d3, respectively. The correlation between the avidity of the binding reaction and the number of C3d's suggests that each C3d in the fusion proteins was capable of interacting with CD21.

In Vivo Antibody Response to (C3d)$_n$-immunogen Fusions

CBA/c male mice of 4–6 weeks of age were obtained from Harlan U.K. Recombinant antigen was diluted in PBS and emulsified in Complete Freunds adjuvant. 0.1 ml was administered intraperitonealy. Alternatively, recombinant antigen was diluted in PBS and 0.1 ml was administered intraperitonealy. Alternatively, recombinant antigen was diluted in PBS and 0.1 ml was administered subcutaneously or intramuscularly, as indicated, on the rear right flank.

Subsequent administrations were done by diluting recombinant antigen in PBS containing 0.1 mg/ml murine albumin (Sigma A-3559).

The antibody response was monitored by obtaining bleeds at intervals from the tail vein of treated mice and assessing HEL specific serum Ig by elisa. Nunc-Immuno plates were coated with HEL (0.5 mg/ml) (Sigma) overnight at 4° C. in carbonate buffer (pH 10.0) and blocked with 1% BSA in PBS. Blocking and all subsequent steps were for 1 h at room temperature. Between steps, the plates were washed three times with PBS containing 0.05% Tween 20. Sera were diluted in 0.1% BSA/PBS and the presence of HEL specific IgG1 was determined using horseradish peroxidase coupled goat anti-mouse IgG1 (Southern Biotechnology Associates Inc.)

A standard curve using pooled sera from mice which had been immunized and boosted with 0.1 mg HEL in CFA and IFA respectively was included on each plate. The elisa was developed with o-phenylenediamine dihydrochloride (Sigma P-9187) and the optical density determined in a Molecular Devices microplate reader at 570 nm.

Dose Response to Immunisation

The relative immunogenicity of HEL was compared to that of HEL-C3d2 and HEL-C3d3 by immunizing mice with incremental amounts of the recombinant proteins subcutaneously in PBS. The highest dose of HEL, 500 pmoles, was the threshold at which unmodified antigen induced an IgG1 response after primary immunization (FIG. 8). In contrast, only 500 fmoles of HEL-C3d2 and 50 fmoles of HEL-C3d3 were required to induce comparable initial IgG1 responses. These doses of the three recombinant proteins also were the threshold amounts necessary for inducing immunologic memory, as indicated by the accelerated and augmented IgG1 responses occurring after challenging primed mice with 50 pmoles of HEL in incomplete Freund's adjuvant (IFA). Furthermore, the generation of immunologic memory to HEL by all recombinant proteins indicates that these responses are T cell-dependent.

Comparison with Complete Freund's Adjuvant

The immune enhancing function of C3d was compared in mice to that of complete Freund's adjuvant (CFA). The threshold doses for eliciting initial IgG1 responses were 50 pmoles for HEL in CFA and 500 fmoles for HEL-C3d3 in PBS, respectively (FIG. 9). The amounts required for inducing memory were 5 pmoles and 50 fmoles for HEL in CFA and HEL-C3d3 in PBS, respectively. Therefore, attaching three molecules of C3d to the antigen is 100-fold more effective in lowering the threshold for acquired immune recognition than is the potent adjuvant, CFA.

Participation of CD21 in vivo

The participation of CD21 in the IgG1 response to HEL-C3d3 was determined. Mice were administered intraperitoneally 300 mg 7G6 anti-CD21 or an isotype-matched control antibody 24 hr before immunization with 500 fmoles of HEL-C3d3 in PBS subcutaneously. The IgG1 anti-HEL titer at day 29 was less than 25 RU for the 7G6-treated mice and 4610 RU for the control mice. Analysis on day 29 by flow cytometry of splenic lymphocytes stained with 7G6 anti-CD21 and 1D3 anti-CD19, respectively, indicated that treatment with 7G6 had eliminated detectable CD21 on B cells without diminishing their expression of CD19. (For FACS analysis, splenocytes were stained with 5 $\mu$g/ml 7G6, 1D3, or control antibody followed by PE-conjugated goat anti-rat F(ab)$_2$ (CalTag).

Specificity of the Response

Mice were co-immunized subcutaneously in PBS with 25 $\mu$g keyhole limpet hemocyanin (KLH) alone or in the presence of 0.5 pmoles HEL-C3d3. The IgG1 response to KLH on day 14 was not altered by the HEL-C3d3, indicating that C3d modifies the response only to the antigen to which it is bound.

Construction and Expression of Murine SmB/SmB-C3d3

Murine SmB cDNA in PGEM 7Zf+ was provided by J. Craft (Yale University). SmB is a protein component of the small ribonucleoprotein particle involved in RNA splicing and is normally only expressed in the cytoplasm. We have been able to express this as a secreted soluble polypeptide fusion with C3d, by transiently transfecting COS cells. The interest in this self-antigen is overcoming tolerance of the immune system using the modulating effect of C3d.

The full SmB sequence was cut from the vector using EcoR1 and the coding sequence amplified by PCR using primers which added a Bgl II restriction site to the 5' end and a BamH1 site to the 3' end of the sequence.

Forward primer (SEQ ID NO 13):
  5'-CGCAGATCTATGACGGTGGGC-3'
Reverse primer (SEQ ID NO 14):
  5'-GCGGGATCCAAGCAGACCTCG-3'

PCR amplification consisted of 35 cycles of 1 minute denaturation, annealing (55° C.) and extension. The PCR product was phenol/chloroform extracted and digested with BamH1 and Bgl II and subcloned into BamH1/Bgl II digested pBS.C3d (see above) to generate pBS.SmB. Colonies were screened for correct orientation by Pvu II restriction digest and the SmB sequence confirmed by dideoxy-mediated sequencing using the Sequenase kit (U.S. Biochemical Corp.).

SmB was then cut from pBS.SmB using BamH1 and Bgl II and subcloned into pSG5.YL (see above) and pSG5.C3d3.YL (see above) opened with BamH1 and Bgl II. Colonies were screened for correct orientation by Pvu II digest. Correct insertion required ligation of the Bgl II site on SmB to the Bam H1 site in the pSG5 vectors and vice versa. These sites are consequently lost which was confirmed by Bam H1 and Bgl II digests. The resulting constructs are pSG5.SmB.YL and pSG5.SmB.C3d3.YL.

Each complete cassette was then cut from the pSGS5 vectors by digestion with EcoR1 and Xba 1, gel purified, extracted and subcloned into pcDNA3 (Invitrogen) which had been previously modified by removal of a 1159 bp Sma 1-Bst 1107 I fragment and then closed. The resulting plasmids were screened by Pvu II restriction digestion and are designated pCMV.SmB.YL and pCMV.SmB.C3d3.YL.

Expression of soluble recombinant protein by the pCMV vectors has been confirmed by transient transfection of COS cells by the DEAE Dextran method. Using in vitro labelling with 35S-methionine appropriately sized proteins for rSmB and rSmB.C3d3 have been immunoprecipitated from COS cell supernatants using the YL½ antibody which recognises the YL epitope on the recombinant proteins.

The results described herein demonstrate that an immune response mounted against an antigen can be modulated by a discrete molecular modification of the antigen, attachment of C3d. The response may be enhanced by a magnitude of 10,000-fold, which is far greater even than enhancement using complete Freund's adjuvant (CFA).

REFERENCES (1) Pepys M B (1974). J. Exp. Med. 140: 126–45.
(2) Ahearn J M, Fearon D T (1989). Adv. Immunol. 46: 183–219.
(3) Law S K, Dodds A W (1990). Biochem. Soc. Trans. 18: 1155–59.
(4) Wolff, et al. Science 247: 1465–1468 (1990).

(5) Tang, et al. Nature 356: 152–154 (1992).
(6) Ulmer J B, et al. Science 259: 1745–1749 (1993). Signal Sequence.
(7) Domdey, et al. Proc. Natl. Acad. Sci. USA 79: 7619–7623 (1982).
(8) Fey, et al. Ann. N.Y. Acad. Sci. 421: 307–312 (1983).
(9) Wehland, et al. EMBO 3: 1295–1300 (1984).
(10) Kilmartin, et al. J. Cell Biol. 9: 576–582 (1983).
(11) Taylor M E, Drickamer, K. Biochem. J., 274: 575–580, (1991).
(12) Jung, et al. Proc. Natl. Acad. Sci. 77: 5759–5743 (1980).
(13) Smith-Gill, et al. J. Immun. 133: 384–393 (1984).
(14) Huston, et al. Meth. Enzymol. 203: 46–88 (1991).
(15) Fearon D T and Carter R H. Annu. Rev. Immunol. 13: 127 (1995).
(16) Tedder T F, et al. Immunol. Today 15: 437 (1994).
(17) Kinoshita T, et al. J. Immunol. 140: 3066 (1988).

What is claimed is:

1. A composition comprising an antigen coupled to a ligand for CD21 (CR2) or CD19, with the proviso that the ligand is not an antibody specific for CD21 or CD19 and that the antigen is not associated with a complement C3 fragment through an ester bond derived from the internal thioester of the complement C3 fragment.

2. A composition according to claim 1 wherein the antigen is a peptide or a polypeptide.

3. A composition according to claim 2 comprising a fusion protein which comprises said antigen and said ligand.

4. A composition according to claim 1 wherein said ligand comprises a C3d molecule.

5. A composition according to claim 4 wherein said ligand comprises more than one C3d molecule.

6. A conjugate comprising an antigen coupled to a C3d molecule, with the proviso that the antigen is not associated with a complement C3 fragment through an ester bond derived from the internal thioester of the complement C3 fragment.

7. A conjugate according to claim 6 comprising more than one C3d molecule.

8. A conjugate according to claim 6 or claim 7 wherein the antigen is a peptide or polypeptide.

9. A conjugate according to claim 8 which is a fusion protein.

10. A fusion protein comprising a peptide or polypeptide antigen linked to a ligand for CD21 (CR2) or CD19 with the proviso that the ligand is not an antibody specific for CD21 or CD19.

11. A fusion protein according to claim 10 wherein said ligand comprises a C3d molecule.

12. A fusion protein according to claim 11 comprising more than one C3d molecule.

13. A method of making a fusion protein comprising a peptide or polypeptide and a ligand of CD21 or CD 19, with the proviso that the ligand is not an antibody specific for CD21 or CD19, the method comprising expression from nucleic acid encoding the fusion protein.

14. A method of making a fusion protein comprising a peptide or polypeptide and one or more C3d molecules, the method comprising expression from nucleic acid encoding the fusion protein.

15. A method according to claim 13 or claim 14 comprising culturing host cells comprising the nucleic acid under conditions for expression of the fusion protein.

16. A composition for administration to an individual, comprising a composition according to claim 1 and a pharmaceutically acceptable excipient or carrier.

17. A composition for administration to an individual, comprising a conjugate comprising an antigen coupled to a C3d molecule and a pharmaceutically acceptable excipient or carrier.

18. A composition according to claim 17 wherein the conjugate comprises more than one C3d molecule.

19. A composition according to claim 17 wherein the antigen is a peptide or polypeptide.

20. A composition according to claim 19 wherein the conjugate is a fusion protein.

21. A composition for administration to an individual, comprising a fusion protein according to claim 10 and a pharmaceutically acceptable excipient or carrier.

22. A method of modulating the immune response of an individual to an antigen of interest, the method comprising administration to the individual of a composition comprising an antigen in association with a ligand for CD21 (CR2) or CD19, with the proviso that the ligand is not an antibody specific for CD21 or CD19 and that the antigen is not associated with a complement C3 fragment through an ester bond derived from the internal thioester of the complement C3 fragment.

23. A method of modulating the immune response of an individual to an antigen of interest, the method comprising administration to the individual of a conjugate comprising the antigen coupled to a C3d molecule.

24. A method according to claim 23 wherein the conjugate comprises more than one C3d molecule.

25. A method according to claim 23 wherein the antigen is a peptide or polypeptide.

26. A method according to claim 25 wherein the conjugate is a fusion protein.

27. A method of modulating the immune response of an individual to an antigen of interest, the method comprising administration to the individual of a fusion protein according to claim 10.

28. A method according to claim 22, claim 23 or claim 27 wherein the immune response comprises an antibody response.

29. A method of raising an antibody response to an antigen of interest which comprises administration to a mammal of a composition comprising the antigen in association with a ligand for CD21 or CD19, with the proviso that the ligand is not an antibody for CD21 or CD19.

30. A method of raising an antibody response to an antigen of interest which comprises administration to a mammal of a conjugate comprising the antigen coupled to a plurality of C3d molecules.

31. A composition according to claim 18 wherein the antigen is a peptide or polypeptide.

32. A composition according to claim 31 wherein the conjugate is a fusion protein.

33. A composition for administration to an individual, comprising a fusion protein according to claim 11 and a pharmaceutically acceptable excipient or carrier.

34. A composition for administration to an individual, comprising a fusion protein according to claim 12 and a pharmaceutically acceptable excipient or carrier.

35. A method according to claim 24 wherein the antigen is a peptide or polypeptide.

36. A method according to claim 35 wherein the conjugate is a fusion protein.

37. A method according to claim 15 wherein the host cells are cultured in a culture medium and the method further comprises isolating the fusion protein from the host cells or the culture medium.

38. A method according to claim 37 wherein the fusion protein is isolated further comprising formulating the isolated fusion protein into a composition comprising a pharmaceutically acceptable excipient or carrier.

* * * * *

SEQUENCE LISTING

```
<160> NUMBER OF SEQ ID NOS: 16

<210> SEQ ID NO: 1
<211> LENGTH: 53
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 1
cactctagac gccgcagatc taccccgca ggctctgggg aacagaacat gat         53

<210> SEQ ID NO: 2
<211> LENGTH: 30
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 2
cgcggatcca ctgctgggga ggtggaagga                                  30

<210> SEQ ID NO; 3
<211> LENGTH: 26
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 3
gatctgaaga gttctgagga tcccgg                                      26

<210> SEQ ID NO: 4
<211> LENGTH: 26
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 4
aattccggga tcctcagaac tcttca                                      26

<210> SEQ ID NO: 5
<211> LENGTH: 24
<212> TYPE: DNA
<213> ORGANISM: Artificial Sequence
<220> FEATURE:
<223> OTHER INFORMATION: Description of Artificial Sequence: synthetic
      oligomer
```

<400> SEQUENCE: 5
gccagatctg gtggaggtgg aagt                                          24

<210> SEQ ID NO: 6
<211> LENGTH: 23
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 6
cgggatccca gccggcagcc tct                                           23

<210> SEQ ID NO: 7
<211> LENGTH: 17
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 7
gcgaattcct agcttgc                                                  17

<210> SEQ ID NO: 8
<211> LENGTH: 23
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 8
gcggatccgg ctcgggtggg cgc                                           23

<210> SEQ ID NO: 9
<211> LENGTH: 23
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 9
gcagatctaa agtctttgga cga                                           23

<210> SEQ ID NO: 10
<211> LENGTH: 23
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 10
cgggatccca gccggcagcc tct                                           23

<210> SEQ ID NO: 11
<211> LENGTH: 18
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 11

```
gatctgaaga cttctgag                                                    18

<210> SEQ ID NO: 12
<211> LENGTH: 18
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 12
gatctgaaga gttctgag                                                    18

<210> SEQ ID NO: 13
<211> LENGTH: 21
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 13
cgcagatcta tgacggtggg c                                                21

<210> SEQ ID NO: 14
<211> LENGTH: 21
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 14
gcgggatcca agcagacctc g                                                21

<210> SEQ ID NO: 15
<211> LENGTH: 5
<212> TYPE: PRT
<213> ORGANISM: Artificial Sequence
<220> FEATURE:
<223> OTHER INFORMATION: Description of Artificial Sequence: peptides
      encoded by genetically engineered nucleic acids

<400> SEQUENCE: 15

Gly Ser Glu Glu Phe
 1               5

<210> SEQ ID NO: 16
<211> LENGTH: 14
<212> TYPE: PRT
<213> ORGANISM: Artificial Sequence
<220> FEATURE:
<223> OTHER INFORMATION: Description of Artificial Sequence: peptides
      encoded by genetically engineered nucleic acids

<400> SEQUENCE: 16

Gly Ser Gly Gly Gly Gly Ser Gly Gly Gly Gly Ser Gly Ser
 1               5                  10
```